(12) United States Patent
Salama

(10) Patent No.: US 8,617,045 B2
(45) Date of Patent: Dec. 31, 2013

(54) URINARY INCONTINENCE DEVICE

(75) Inventor: Fouad A. Salama, Temecula, CA (US)

(73) Assignee: International Medical Technology, Inc., Temecula, CA (US)

( * ) Notice: Subject to any disclaimer, the term of this patent is extended or adjusted under 35 U.S.C. 154(b) by 2232 days.

(21) Appl. No.: 11/464,686

(22) Filed: Aug. 15, 2006

(65) Prior Publication Data

US 2008/0045781 A1 Feb. 21, 2008

(51) Int. Cl.
*A61F 2/00* (2006.01)
(52) U.S. Cl.
USPC .............................................................. 600/29
(58) Field of Classification Search
USPC ............... 600/29–32; 606/219, 108; 128/885; 623/1.15, 23.64–23.67; 604/102.01
See application file for complete search history.

(56) References Cited

U.S. PATENT DOCUMENTS

| | | | |
|---|---|---|---|
| 3,211,150 A | 10/1965 | Foderick | |
| 4,968,294 A | 11/1990 | Salama | |
| 5,306,226 A | 4/1994 | Salama | |
| 5,360,403 A | 11/1994 | Mische | |
| 5,447,497 A | 9/1995 | Sogard et al. | |
| 5,545,209 A * | 8/1996 | Roberts et al. | 623/1.11 |
| 5,569,216 A | 10/1996 | Kim | |
| 5,634,877 A | 6/1997 | Salama | |
| 5,693,001 A | 12/1997 | Salama | |
| 5,704,913 A | 1/1998 | Abele et al. | |
| 5,792,042 A * | 8/1998 | Cohen et al. | 600/29 |
| 5,800,339 A | 9/1998 | Salama | |
| 5,893,826 A | 4/1999 | Salama | |
| 6,033,390 A | 3/2000 | von Dyck | |
| 6,126,634 A | 10/2000 | Bagaoisan et al. | |
| 6,168,602 B1 | 1/2001 | Ryan | |
| 6,171,230 B1 | 1/2001 | Hakky et al. | |
| 6,527,755 B1 | 3/2003 | Salama | |
| 6,746,465 B2 | 6/2004 | Diederich et al. | |
| 6,974,475 B1 | 12/2005 | Wall | |
| 2004/0044307 A1 | 3/2004 | Richardson et al. | |
| 2004/0044397 A1 | 3/2004 | Stinson | |
| 2004/0181235 A1 | 9/2004 | Daignault et al. | |
| 2004/0249343 A1 * | 12/2004 | Cioanta | 604/113 |

FOREIGN PATENT DOCUMENTS

| | | |
|---|---|---|
| WO | 94/26215 A | 11/1994 |
| WO | 98/05267 A | 2/1998 |

OTHER PUBLICATIONS

International Search Report in co-pending PCT/US2007/018122 mailed Jan. 28, 2008.

* cited by examiner

*Primary Examiner* — Christine Matthews
(74) *Attorney, Agent, or Firm* — McKee, Voorhees & Sease, P.L.C.

(57) ABSTRACT

A urinary control device for sealing off at a neck and along the inside wall of a bladder to prevent leaking and dislodging of the device from within the bladder is disclosed. The device includes an inner tubular member. The device also includes an expandable sealing member. A deployable stiffening member is positioned within the expandable sealing member. The stiffening member expands within the expandable sealing member to erect and shape the expandable sealing member. The deployable stiffening member strengthens the expandable sealing member, retaining the device within the bladder and sealing off the bladder against leaking.

23 Claims, 13 Drawing Sheets

URINARY INCONTINENCE DEVICE

BACKGROUND OF THE INVENTION

Persons experiencing an inability to control the passage of urine ranging from an occasional leakage of urine, to a complete inability to hold any urine have need for a urinary control device that will not leak and is simple to install, operate and remove.

Incontinence is a problem for many people including older adults. Present day approaches for dealing with incontinence such as the Foley catheter often times cause urinary tract infections. A bag for urine is required and smell becomes a problem. The chances of infection are increased each time the bag is changed. The cost for the Foley catheters and bags is substantial. An inflatable conventional spherical balloon is used to keep the catheter in the bladder, but leakage around the catheter occurs and is a problem. It was not an object of this product to provide a seal around the catheter at the bladder orifice.

What is needed is a simple inexpensive device for controlling urine flow through the urethra which is compatible to the body and will not cause discomfort, infection and pass urine but only by operation of the valve rather than around the outside of the catheter.

BRIEF SUMMARY OF THE INVENTION

Therefore it is a primary object, feature, or advantage of the present invention to improve over the state of the art by providing a urinary incontinence device that meets the needs of persons experiencing an inability to control the passage of urine.

It is a further object, feature, or advantage of the present invention to provide a urinary incontinence device wherein the sealing member within the bladder has a varying outer perimeter to accommodate different sized urethras, at the neck of the bladder.

It is a still further object, feature, or advantage of the present invention to provide a urinary incontinence device that provides a pump with living hinges having a tactile surface operable by squeezing or touching for sealing the sealing member whether the device is within view or out of view.

Another object, feature, or advantage of the present invention to provide a urinary incontinence device having a flat and smooth distal end at the entrance to the urethra that does not interfere with sexual intercourse.

Yet another object, feature, or advantage of the present invention to provide a urinary incontinence device having an adjustable and expandable sealing member encapsulated by a gel cap for easy and comfortable insertion.

A further object, feature, or advantage of the present invention to provide a urinary incontinence device wherein the sealing member provides a soft and smooth contact surface for increased comfort.

It is a further object, feature, or advantage of the present invention to provide a urinary incontinence device having a balloon valve positioned within a separate coupling member that attaches to the outer end of the tube for selectively passing urine from the bladder.

Another object, feature, or advantage of the present invention is to provide a urinary incontinence device wherein the coupling member having the balloon valve for selectively passing urine is adapted to fit each embodiment of the urinary incontinence device.

Yet another object, feature, or advantage of the present invention is to provide a urinary incontinence device designed to prevent contamination of the sealing member.

A still further object, feature, or advantage of the present invention is to provide a urinary incontinence device that prevents leaking by sealing off at the neck and along the inside wall of the bladder using an expandable umbrella shaped balloon.

Another object, feature, or advantage of the present invention is to provide a urinary incontinence device that prevents leaking by sealing off at the neck and along the inside wall of the bladder using an expandable umbrella shaped balloon and a second balloon for seating, securing and retaining the expandable umbrella shaped balloon within and against the inside wall of the bladder.

Yet another object, feature, or advantage of the present invention is to provide a urinary incontinence device wherein the umbrella shaped member for sealing off at the neck and along the inside wall of the bladder is erected and shaped by an umbrella shaped balloon within the umbrella shaped member.

A further object, feature, or advantage of the present invention is to provide a urinary incontinence device wherein the umbrella shaped member is erected and shaped to an open position within the bladder by a wire frame within the umbrella shaped member.

Another object, feature or advantage of the present invention is to provide a urinary incontinence device wherein the wire frame within the umbrella shaped member is encapsulated in the gel cap and opens to the expanded sealing position upon dissolution of the encapsulated gel cap.

Yet another object, feature, or advantage of the present invention is to provide a urinary incontinence device wherein the sealing member is coaxial with the urine drain tube during insertion and expanded by a deployable stiffening member after insertion.

A still further object, feature, or advantage of the present invention is to provide a urinary incontinence device that uses as the deployable stiffening member a balloon positioned between the sealing member and urine drain tube to expand the sealing member radially outward from the urine tube in sealing contact at the neck and along the inner wall of the bladder.

Another object, feature, or advantage of the present invention is to provide a urinary incontinence device wherein the sidewall of the sealing member has an annular thinned wall portion to assist expansion of the sealing member along the annular thinned wall portion radially outward away from the urine drain tube.

A further object, feature, or advantage of the present invention is to provide a urinary incontinence device wherein the annular thinned wall portion may be positioned either on the outer or inner surface of the sealing member.

Still another object, feature, or advantage of the present invention is to provide a urinary incontinence device wherein the annular thinned wall portion may be positioned on the main balloon.

Yet another object, feature, or advantage of the present invention is to provide a urinary incontinence device wherein the sealing member is erected and shaped to a sealing position within the bladder using a deployable stiffening member.

A still further object, feature, or advantage of the present invention is to provide a urinary incontinence device wherein a coupling device for attaching to the urine tube has a pump to inflate and deflate a balloon within the urine tube of the coupling device for selectively passing urine.

Yet another object, feature, or advantage of the present invention is to provide a urinary incontinence device wherein the pump deflates the inflatable balloon within the urine tube of the coupling device from a normally closed inflated condition.

According to one aspect of the present invention a urinary control device for sealing off at a neck and along the inside wall of a bladder to prevent leaking and dislodging of the device from within the bladder is disclosed. The device includes an inner tubular member for transporting urine from the bladder, an inflatable balloon surrounding the inner tubular member, and an expandable outer tubular member covering the inflatable balloon and attached to the inner tubular member. The device also includes an annular thinned wall portion in the expandable outer tubular member. The inflatable balloon when inflated expands the annular thinned wall portion on the expandable outer tubular member radially outward and away from the inner tubular member for sealing and retaining the expandable outer tubular member against the neck and inner wall of the bladder to prevent leaking.

According to another feature of the present invention, the expandable outer tubular member having first and second ends fixedly attached to the inner tubular member. The outer tubular member having slack between the first and second ends to thereby assist expansion of the annular thinned wall portion radially outward and away from the tubular member.

According to another feature of the present invention, the inflatable balloon is positioned and expanded between the inner and outer tubular members.

According to another feature of the present invention, the inflatable balloon is positioned between the first and second ends of the expandable outer tubular member.

According to another feature of the present invention, the annular thinned wall portion on the expandable outer tubular member is operational between a collapsed shape being coaxial with the inner tubular member and an expanded shape forming a seal between the expandable outer tubular member and the neck and inner wall of the bladder by inflating and deflating the inflatable balloon.

According to another aspect of the present invention a urinary control device for sealing off at a neck and along the inside wall of a bladder to prevent leaking and dislodging of the device from within the bladder is disclosed. The device includes a tubular member having inner and outer ends interconnected by a passageway. The tubular member has a sidewall with inner and outer surfaces. The passageway being defined by the inner sidewall surface. The device also includes an inflatable balloon having a central passageway. The outer sidewall surface of the tubular member being surrounded by the central passageway of the inflatable balloon. The device includes as well an expandable outermost tubular member in covering relation to the inflatable balloon. The expandable outermost tubular member has a first and second opposite end fixedly attached to the outer sidewall surface of the tubular member. Also included is an annular thinned wall portion between the first and second opposite end on the expandable outermost tubular member. The annular thinned wall portion operational between a collapsed shape being coaxial with the tubular member and an expanded shape forming a seal between the outermost tubular member and the neck and inner wall of the bladder.

According to another feature of the present invention, the annular thinned wall portion for encouraging expansion of the expandable outermost tubular member along the annular thinned wall portion.

According to another aspect of the present invention a urinary control device for sealing off at a neck and along the inside wall of a bladder to prevent leaking and dislodging of the device from within the bladder is disclosed. The device includes an inner tubular member having an inner and an outer end interconnected by a passageway. The inner tubular member has an inner and outer sidewall. The device includes as well an expandable sealing member having an inner surface, an outer surface, a proximal end fixedly attached to the outer sidewall of the inner tubular member and an expandable perimeter operational between a collapsed closed shape being coaxial with the inner tubular member and an expanded open shape to seal the outer surface of the expandable sealing member against the inner wall and neck of the bladder for preventing urine from leaking from the bladder. The device also includes a deployable stiffening member positioned within the expandable sealing member. The stiffening member expands within the expandable sealing member for erecting and shaping the expandable sealing member. The deployable stiffening member assists in strengthening the expandable sealing member, retaining the device within the bladder and sealing off the bladder against leaking.

According to another feature of the present invention, the expandable sealing member is an umbrella shaped member and the deployable stiffening member is an inflatable umbrella shaped balloon formed within and by the umbrella shaped member.

According to another feature of the present invention, the expandable perimeter is a free outer end opposite the proximal end on the umbrella shaped member.

According to another feature of the present invention, the inflatable umbrella shaped balloon within the umbrella shaped member is operational between inflated and deflated conditions. The inflatable umbrella shaped balloon when inflated erecting and shaping the umbrella shaped member and seating the outer surface of the umbrella shaped member against the inside wall and neck of the bladder to prevent leaking.

According to another feature of the present invention, the device has a second inflatable balloon positioned at the inner end and around the outer sidewall of the inner tubular member for operation between inflated and deflated conditions. The second inflatable balloon when inflated pressing against the inner surface of the umbrella shaped member for retaining the device within the bladder and maintaining sealing engagement between the outer surface of the umbrella shaped member and the inside wall and neck of the bladder to prevent leaking.

According to another feature of the present invention, a dissolvable gel cap encapsulates the outer surface of the umbrella shaped member for inserting the device.

According to another feature of the present invention, the free outer end of the umbrella shaped member expands radially outward from the collapsed closed shape.

According to another feature of the present invention, the inner tubular member having an inflation conduit extending between the inflatable umbrella shaped balloon and the outer end of the inner tubular member.

According to another feature of the present invention, the inner tubular member having a second inflation conduit extending between the second inflatable balloon and the outer end of the inner tubular member.

According to another feature of the present invention, the inner tubular member is measured and cut to the length of the urethra.

According to another feature of the present invention, the device has a coupling member inserted into the outer end of the inner tubular member.

According to another feature of the present invention, the coupling member having a passageway with a center and an inner sidewall surface for passing urine there-through.

According to another feature of the present invention, the coupling member further comprises an inflatable balloon valve positioned within the passageway of the coupling member for selectively passing urine there-through.

According to another feature of the present invention, the inflatable balloon valve is attached about the entire circumference of the inner sidewall surface of the passageway and when inflated expands radially inward away from the inner sidewall surface toward the center of the passageway in sealing engagement with itself.

According to another feature of the present invention, the coupling member having a pump and inflation conduit in fluid communication with the inflatable balloon valve for deflating the inflatable balloon valve from a normally closed position to an open position where the inflatable balloon is coaxial with the inner sidewall surface of the passageway for passing urine there-through.

According to another feature of the present invention, the pump comprising a pump casing in fluid communication with the inflation conduit and inflatable balloon valve, the pump further comprising a pair of living hinges adapted for connection to a plunger to thereby assist movement of the plunger within pump casing.

According to another feature of the present invention, the living hinges being pressed and held inward toward the plunger for drawing the plunger out of the pump casing and evacuating the inflatable balloon valve thereby collapsing the inflatable balloon valve and allowing urine to pass thereby.

According to another feature of the present invention, the living hinges being released and automatically flexing outward away from the plunger for pushing the plunger into the pump casing and inflating the inflatable balloon valve.

According to another feature of the present invention, the coupling member further comprising at least one check valve having at least one inflation conduit in fluid communication with the inflatable umbrella shaped balloon and second inflatable balloon for separately inflating the balloons using a syringe.

According to another feature of the present invention, the expandable sealing member is an expandable outermost tubular member and the deployable stiffening member is an inflatable balloon within the outermost tubular member.

According to another feature of the present invention, the expandable outermost tubular member having a first and second opposite end fixedly attached to the outer sidewall of the inner tubular member. The outer tubular member has slack between the first and second ends to thereby assist expansion of the annular thinned wall portion radially outward and away from the tubular member.

According to another feature of the present invention, the expandable perimeter is an annular thinned wall portion on the outermost tubular member between the first and second opposite end. The inflatable balloon when inflated expands the annular thinned wall portion on the outermost tubular member radially outward and away from the outer sidewall of the inner tubular member for sealing and retaining the outermost tubular member against the neck and inner wall of the bladder.

According to another feature of the present invention, the inflatable balloon is positioned and expanded between the inner and outermost tubular members.

According to another feature of the present invention, the inner tubular member has an inflation conduit extending between the inflatable balloon and the outer end of the inner tubular member.

According to another feature of the present invention, the inner tubular member is measured and cut to the length of the urethra.

According to another feature of the present invention, having a coupling member inserted into the outer end of the inner tubular member.

According to another feature of the present invention, the coupling member having a passageway with a center and an inner sidewall surface for passing urine there-through.

According to another feature of the present invention, the coupling member further comprises an inflatable balloon valve positioned within the passageway of the coupling member for selectively passing urine there-through.

According to another feature of the present invention, the inflatable balloon valve is attached about the entire circumference of the inner sidewall surface of the passageway and when inflated expands radially inward away from the inner sidewall surface toward the center of the passageway in sealing engagement with itself.

According to another feature of the present invention, the coupling member having a pump and inflation conduit in fluid communication with the inflatable balloon valve for deflating the inflatable balloon valve from a normally closed position to an open position where the inflatable balloon is coaxial with the inner sidewall surface of the passageway for passing urine there-through.

According to another feature of the present invention, the pump comprises a pump casing in fluid communication with the inflation conduit and inflatable balloon valve. The pump further comprises a pair of living hinges adapted for connection to a plunger to thereby assist movement of the plunger within the pump casing.

According to another feature of the present invention, the living hinges being pressed and held inward toward the plunger for drawing the plunger out of the pump casing and evacuating the inflatable balloon valve thereby collapsing the inflatable balloon valve and allowing urine to pass thereby.

According to another feature of the present invention, the living hinges being released and automatically flexing outward away from the plunger for pushing the plunger into the pump casing and inflating the inflatable balloon valve.

According to another feature of the present invention, the coupling member further comprises at least one check valve having at least one inflation conduit in fluid communication with the inflatable balloon for inflating the balloon using a syringe.

According to another feature of the present invention, the expandable sealing member is an umbrella shaped member and the deployable stiffening member is a wire frame within the umbrella shaped member.

According to another feature of the present invention, the expandable perimeter is a free outer end opposite the proximal end on the umbrella shaped member.

According to another feature of the present invention, the wire frame positioned within the umbrella shaped member is operational between collapsed and expanded conditions. The wire frame when expanded erecting and shaping the umbrella shaped member and seating the outer surface of the umbrella shaped member against the inside wall and neck of the bladder to prevent leaking.

According to another feature of the present invention, the wire frame is a continuous wire frame and expands to a normally expanded open condition upon dissolution of the gel cap.

According to another aspect of the present invention a urinary control device for sealing off at a neck and along the inside wall of a bladder to prevent leaking and dislodging of the device from within the bladder is disclosed. The device includes an inner tubular member having an inner and an outer end interconnected by a passageway. The inner tubular member has an inner and outer sidewall. The device also includes an expandable umbrella shaped member having an inner surface, an outer surface, a proximal end fixedly attached to the outer sidewall of the inner tubular member and an opposite free outer end operational between a collapsed closed shape being coaxial with the inner tubular member and an expanded open shape to seal the outer surface of the expandable umbrella shaped member against the inside wall and neck of the bladder for preventing urine from leaking from the bladder. The device further includes an inflatable umbrella shaped balloon formed within and by the expandable umbrella shaped member, inflatable umbrella shaped balloon being operational between inflated and deflated conditions, the inflatable umbrella shaped balloon when inflated erecting and shaping the expandable umbrella shaped member to thereby assist in strengthening the expandable umbrella shaped member, retaining the device within the bladder and seating the outer surface of the expandable umbrella shaped member against the inside wall and neck of the bladder to prevent leaking.

According to another feature of the present invention, the device has a second inflatable balloon positioned at the inner end and around the outer sidewall of the inner tubular member for operation between inflated and deflated conditions. The second inflatable balloon when inflated presses against the inner surface of the expandable umbrella shaped member for retaining the device within the bladder and maintaining sealing engagement between the outer surface of the expandable umbrella shaped member and the inside wall and neck of the bladder to prevent leaking.

According to another aspect of the present invention a method for sealing off at a neck and along the inside wall of a bladder to prevent leaking and dislodging of the device from within the bladder is disclosed. The method includes providing an inner tubular member having an inner and an outer end interconnected by a passageway, the inner tubular member having an inner and outer sidewall. The method also includes expanding an expandable sealing member having an inner surface, an outer surface, a proximal end fixedly attached to the outer sidewall of the inner tubular member and an expandable perimeter on the sealing member operational between a collapsed closed shape being coaxial with the inner tubular member and an expanded open shape to seal the outer surface of the expandable sealing member against the inner wall and neck of the bladder for preventing urine from leaking from the bladder. The method further includes deploying a deployable stiffening member positioned within the expandable sealing member. The stiffening member expands within the expandable sealing member for erecting and shaping the expandable sealing member. The deployable stiffening member assists in strengthening the expandable sealing member, retaining the device within the bladder and sealing off the bladder against leaking.

According to another feature of the present invention, positioning a second inflatable balloon at the inner end and around the outer sidewall of the inner tubular member for operation between inflated and deflated conditions. The second inflatable balloon when inflated presses against the inner surface of the expandable umbrella shaped member for retaining the device within the bladder and maintaining sealing engagement between the outer surface of the expandable umbrella shaped member and the inside wall and neck of the bladder to prevent leaking.

According to another feature of the present invention, the inner tubular member is measured and cut to the length of the urethra.

According to another feature of the present invention, a coupling member is inserted into the outer end of the inner tubular member.

According to another feature of the present invention, the coupling member has a passageway with a center and an inner sidewall surface for passing urine there-through.

According to another feature of the present invention, the coupling member further comprises an inflatable balloon valve positioned within the passageway of the coupling member for selectively passing urine there-through.

According to another feature of the present invention, the inflatable balloon valve is attached about the entire circumference of the inner sidewall surface of the passageway and when inflated expands radially inward away from the inner sidewall surface toward the center of the passageway in sealing engagement with itself.

According to another feature of the present invention, the coupling member having a pump and inflation conduit in fluid communication with the inflatable balloon valve for deflating the inflatable balloon valve from a normally closed position to an open position where the inflatable balloon is coaxial with the inner sidewall surface of the passageway for passing urine there-through.

According to another feature of the present invention, the pump comprises a pump casing in fluid communication with the inflation conduit and inflatable balloon valve. The pump further comprises a pair of living hinges adapted for connection to a plunger to assist movement of the plunger within pump casing.

According to another feature of the present invention, the living hinges being pressed and held inward toward the plunger for drawing the plunger out of the pump casing and evacuating the inflatable balloon valve thereby collapsing the inflatable balloon valve and allowing urine to pass thereby.

According to another feature of the present invention, the living hinges being released and automatically flexing outward away from the plunger for pushing the plunger into the pump casing and inflating the inflatable balloon valve.

According to another feature of the present invention, the coupling member further comprises at least one check valve having at least one inflation conduit in fluid communication with the inflatable umbrella shaped balloon and second inflatable balloon for separately inflating the balloons using a syringe.

One or more of these and/or other objects, features, or advantages of the present invention will become apparent from the specification and claims that follow.

BRIEF DESCRIPTION OF THE DRAWINGS

FIG. 1A is an exploded view of the annular thin portion taken along lines 1A-1A from FIG. 1.

DETAILED DESCRIPTION OF THE DRAWINGS

Figure 1:
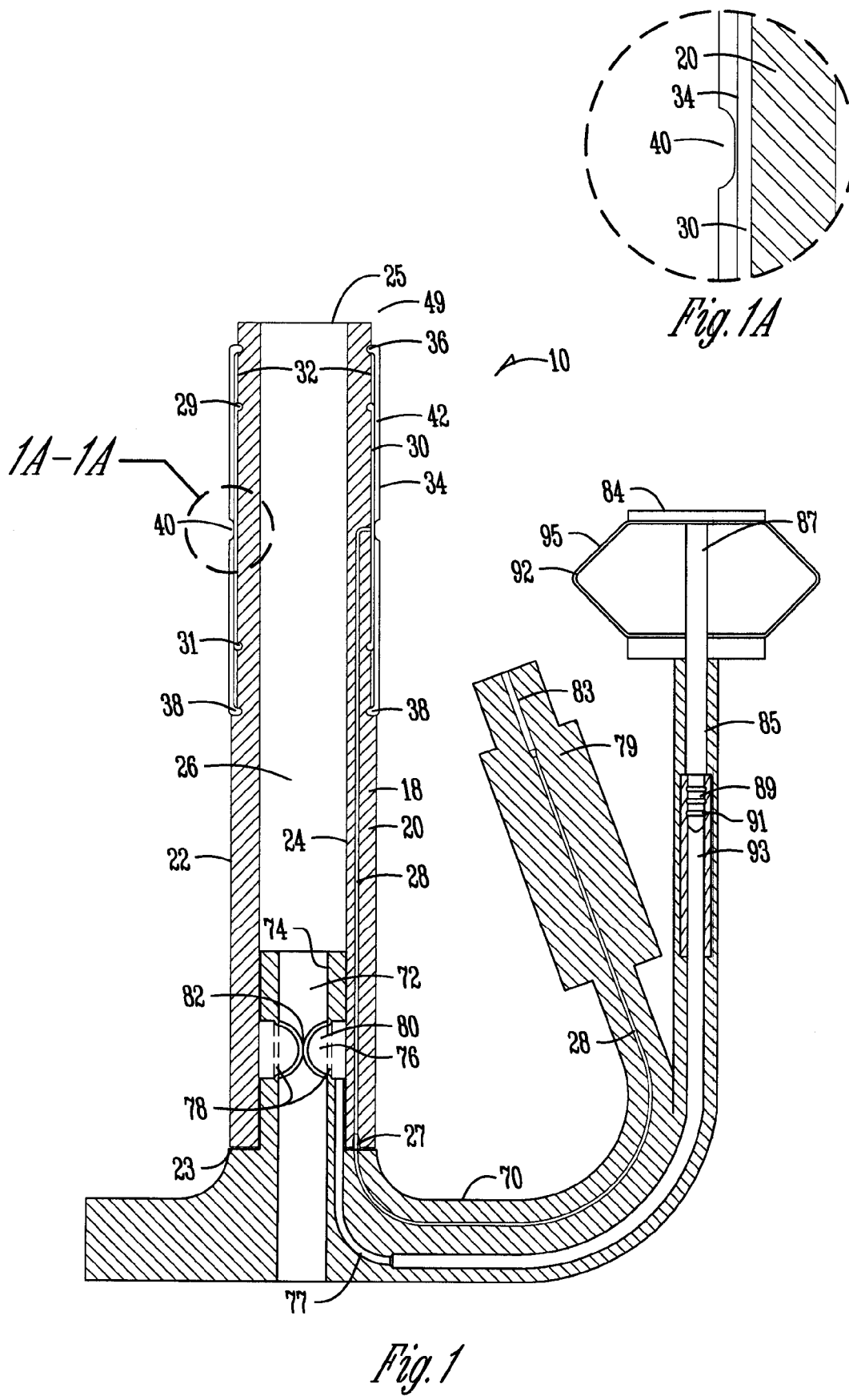
FIG. 1 is a front view of one embodiment of the control device.
Figure 2:
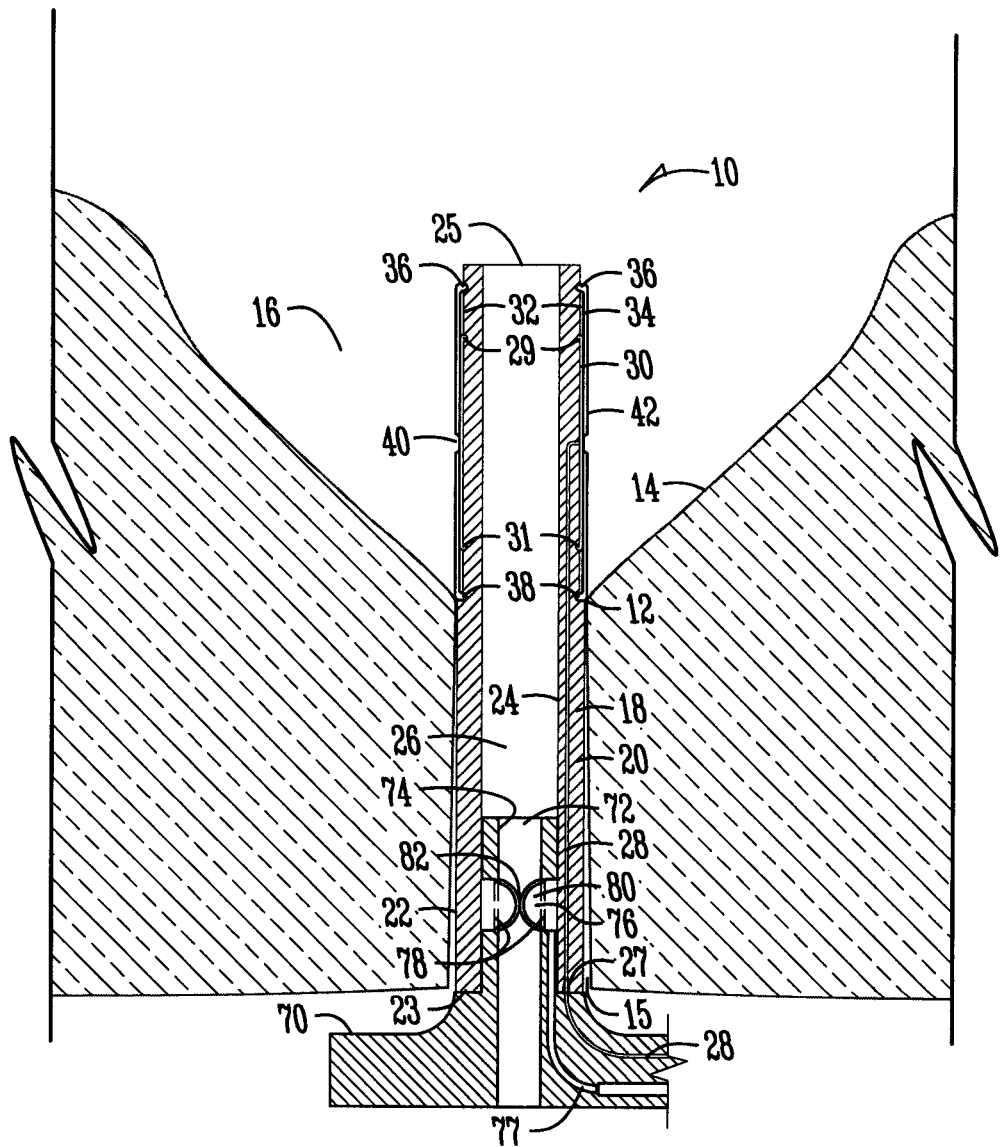
FIG. 2 is a cross-sectional view of one embodiment of the control device positioned in a bladder.

The present invention includes a number of aspects all of which have broad and far reaching applications. Although specific embodiments are described herein, the present invention is not limited to the specific embodiments. One aspect of the invention relates to the use of an expandable membrane for sealing off at the neck and along the inside wall of the bladder. The expandable membrane is deployable using balloons and other devices for erecting and shaping the expandable membrane into a sealing position. The invention includes also a coupling member with a balloon valve for selectively passing urine from the bladder.

Turning now to the drawings in which similar reference characters denote similar elements through the several views. Illustrated in FIGS. 1-13 is the combination of various views and in use configurations of a urinary incontinence and coupling device.

FIG. 1 is a front view of one embodiment of the control device. In FIG. 1, the urinary control device is shown having a tubular member 18. The tubular member 18 has inner 25 and outer 23 ends interconnected by a passageway 26. The tubular member 18 also has a sidewall 20 with inner 24 and outer 22 surfaces. The passageway 26 within tubular member 18 is defined by the inner 24 sidewall surface. Also shown is an inflatable balloon 30 having a central passageway 32. The central passageway 32 in the inflatable balloon 30 surrounds the outer 22 sidewall 20 surface of the tubular member 18. Also shown is an expandable outermost tubular member 34 covering the inflatable balloon 30 and attached to the outer surface 22 of the tubular member 18. The expandable outermost tubular member 34 has a first end 36 and a second opposite end 38 that are fixedly attached to the outer 22 sidewall 20 surface of the tubular member 18. Shown on the expandable outermost tubular member 34 is an annular thinned wall portion 40 positioned between the first 36 and second 38 opposite end on the outermost tubular member 34. The annular thinned wall portion is preferably 1-2 mm across, as best shown in FIG. 1A, to encourage deformation and expansion of the outermost tubular member 34 along the annular thinned wall portion 40. The annular thinned wall portion 40 on the outermost tubular member 34 is operational between a collapsed shape 42 being coaxial with the tubular member 18 and an expanded shape 44 forming a seal 46 between the expandable outermost tubular member 34 and the neck 12 and inner wall 14 of the bladder 16. Before the urinary control device 10 is inserted, the inner tubular member 18 is measured and cut to the length of the urethra 15. A coupling member 70 is inserted into the outer end 23 of the inner tubular member 18. The coupling member 70 has a passageway 72 with an inner sidewall surface 74 for passing urine there-through. The coupling member 70 also has an inflatable balloon valve 76 positioned within the passageway 72 of the coupling member 70 for selectively passing urine there-through. The inflatable balloon valve 76 is attached about the entire circumference 78 of the inner sidewall surface 74 of the passageway 72. When the inflated balloon valve 76 is in the normally closed inflated 80 position, the inflatable balloon valve 76 is expanded radially inward away from the inner surface 74 of the passageway 72 toward the center 82 of the passageway 70 in sealing engagement with itself. The inflatable balloon valve 76 in the inflated position 80 prevents urine from passing through the passageway 72 from within the bladder 16.

A pump 84, as shown, is used to inflate and deflate the inflatable balloon valve 76 for selectively passing urine through the passageway 72 from the bladder 16. The inflatable balloon valve 76 is by default kept in the normally closed inflated condition 80.

The inflatable balloon 30 is expanded after the device 10 is inserted. To inflate the inflatable balloon 30 an inflation conduit 28 extends between the inflatable balloon 30 and the outer ends 23 of the inner tubular member 18. The coupling member 70 contains a coupling 27 for connecting the inflation conduit 28 in the inner tubular member 18 to the inflation conduit 28 in the coupling member 70. As part of the coupling member 70, a check valve 79 is connected to the inflation conduit 28 thereby providing fluid communication to the inflatable balloon 30. Thus, by use of a syringe or any other injectable means, saline is injected through the insert 83 in the check valve 79 and inflation conduit 28 to inflate the inflatable balloon 30.

Figure 3:
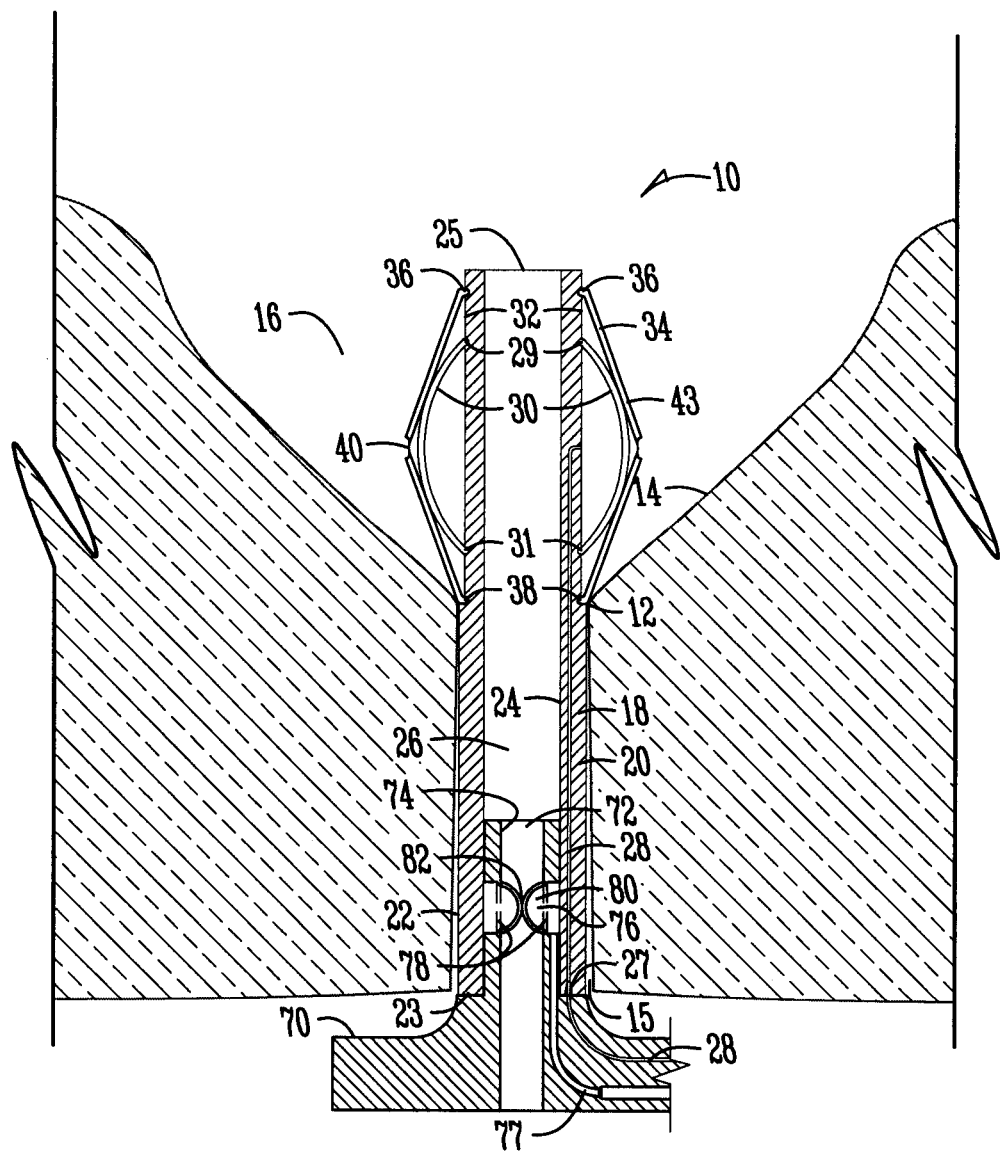
FIG. 3 is a cross-sectional view of one embodiment of the control device positioned in a bladder with the outer member having been partially expanded.

FIG. 3 is a cross sectional of one embodiment of the control device positioned in a bladder with an outer member having been partially expanded. In FIG. 3, the inflatable balloon 30 is partially inflated. The inflatable balloon 30 is positioned and expanded between the inner 18 and outermost tubular member 34. The inflatable balloon 30 is attached to the outer sidewall 22 of the inner tubular member 18. Thus, as the inflatable balloon is inflated the annular thinned wall portion 40 on the outermost tubular member 34 encourages expansion of the outermost tubular member 34 along the annular thinned wall portion 40 radially outward and away from the outer sidewall 22 of the inner tubular member 18. As the annular thinned wall portion 40 expands radially outward slack in the outermost tubular member 34 between the first 36 and second end 38 is taken up in the outward expansion of the outermost tubular member along the annular thinned wall portion 34. The annular thinned portion 40 expands with the inflatable balloon 30 away from the outer sidewall 22 of the inner tubular member 18 to seal against the neck 12 and inner wall 14 of the bladder 16. The annular thinned wall portion 40, along with the outermost tubular member 34 having slack in the member 34 between the first 36 and second opposite end 38, allows the outermost tubular member 34 to expand to accommodate retention and sealing in larger diameter urethras.

Figure 4:
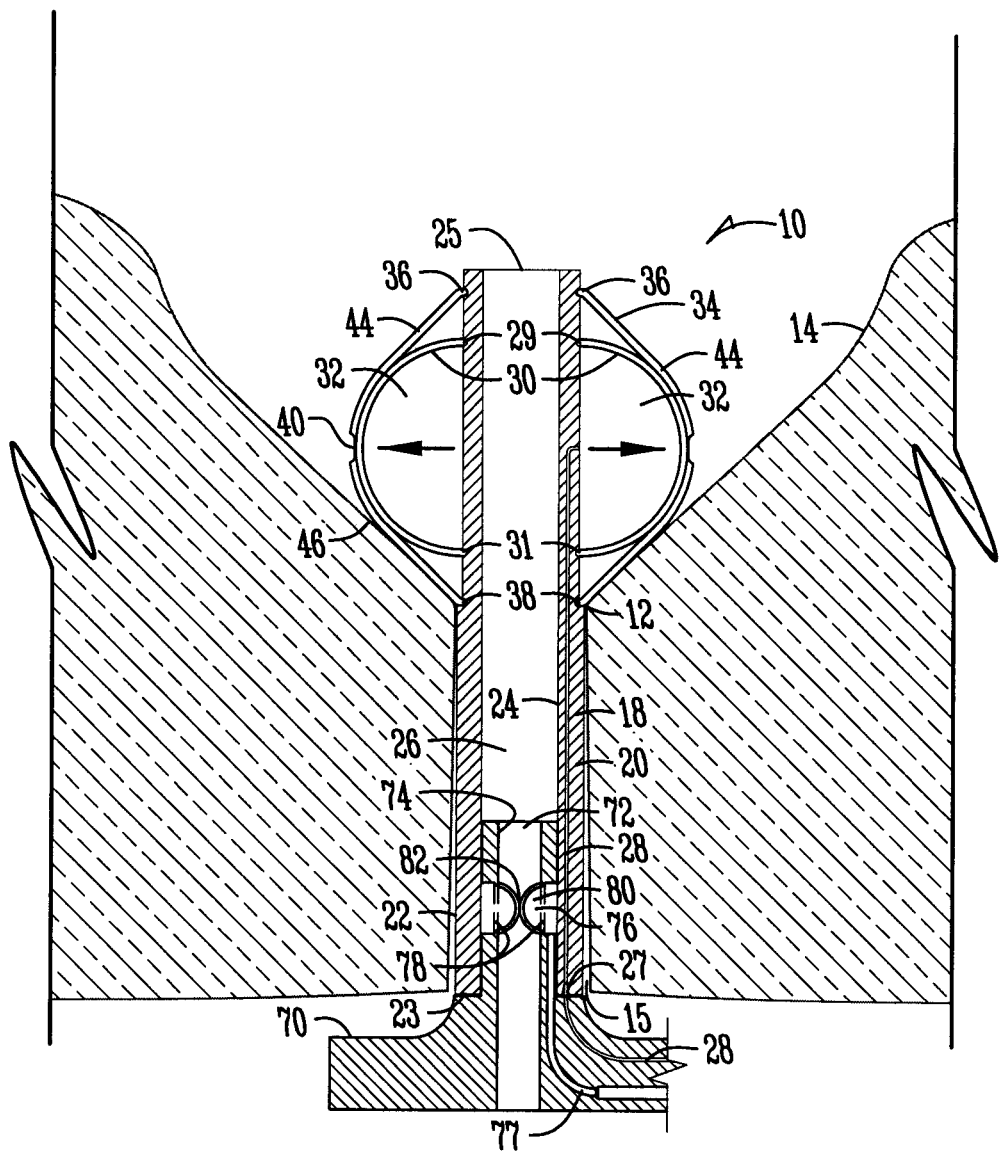
FIG. 4 is a cross-sectional view of one embodiment of the control device positioned in a bladder with the outer member having been fully expanded.

FIG. 4 is cross sectional view of one embodiment of the control device positioned in a bladder with the outer member having been fully expanded. In FIG. 4, the inflatable balloon 30 has been expanded to the position where the annular thinned wall portion 40 on the outermost tubular member 34 creates a seal 46 between the outermost tubular member 34 and the neck 12 and inner wall 14 of the bladder 16.

Figure 5:
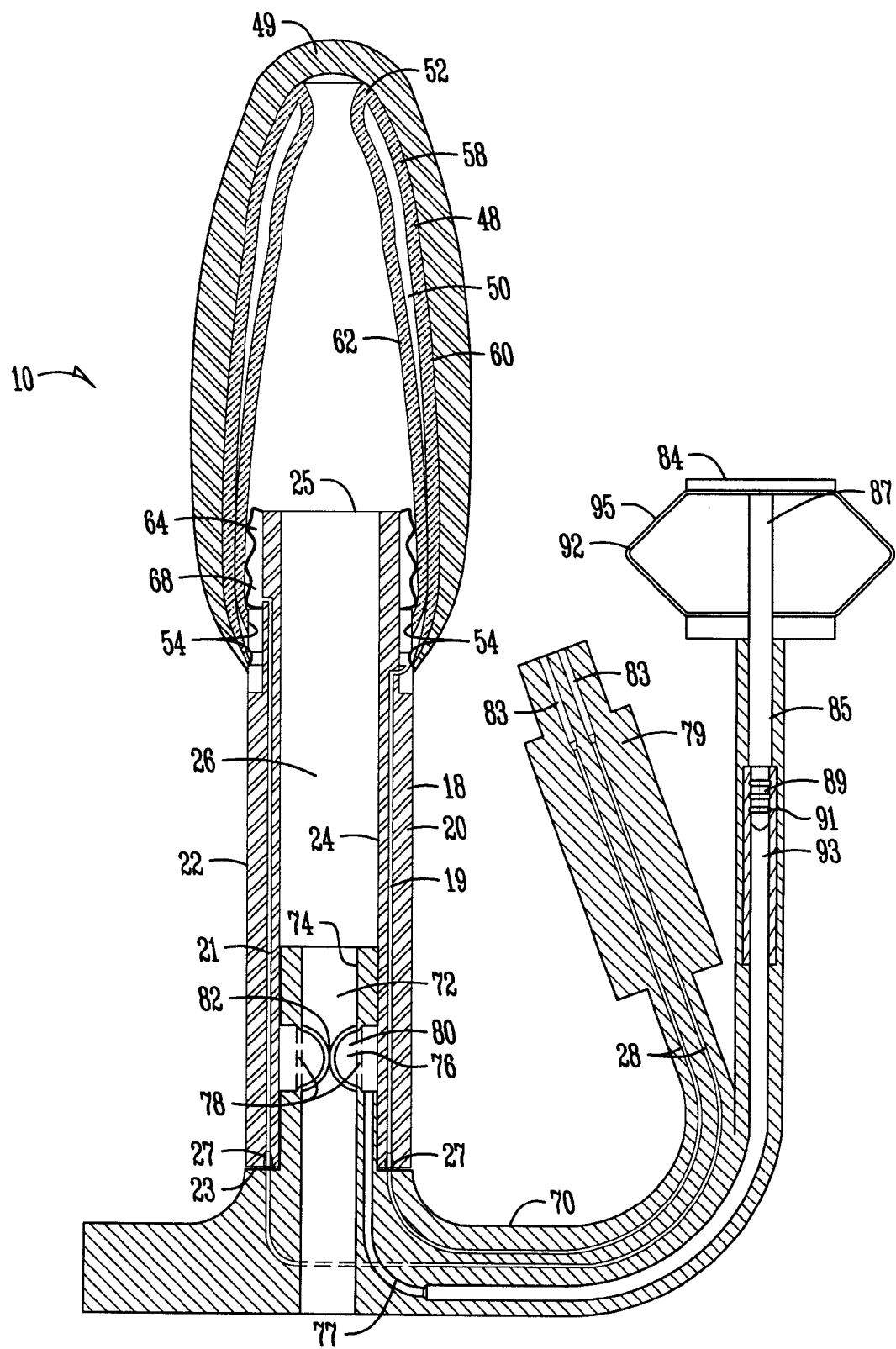
FIG. 5 is a front view of another embodiment of the control device.

FIG. 5 is a front view of another embodiment of the control device. In FIG. 4, the slack between opposite ends 36, 38 in the outermost tubular member 34 has been taken up in the expansion of the inflatable balloon 30.

Figure 6:
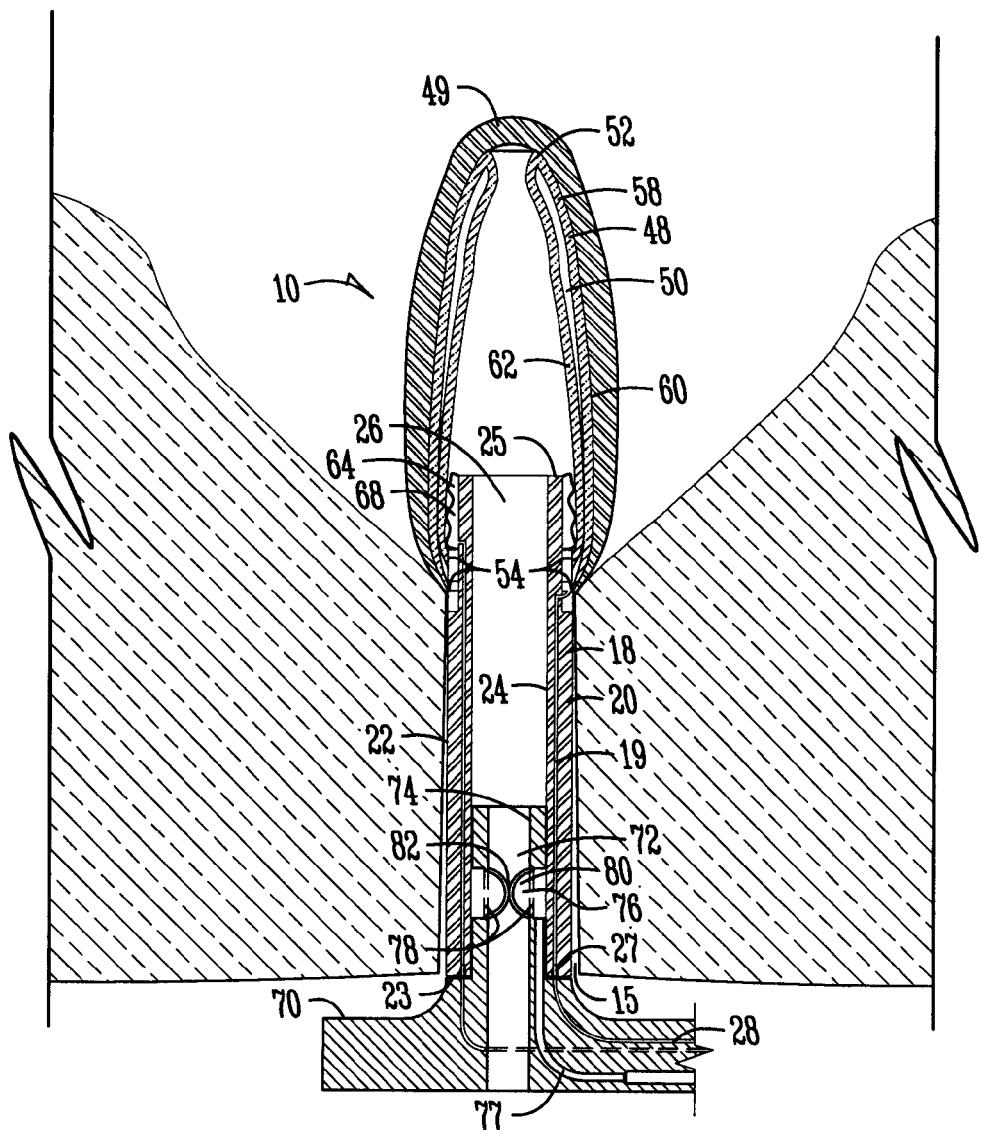
FIG. 6 is a cross-sectional view of another embodiment of the control device positioned in a bladder.

FIG. 5 is a front view of another embodiment of the control device. In FIG. 5, the expandable sealing member is shown as an umbrella shaped member 48 and the deployable stiffening member is shown as an inflatable umbrella shaped balloon 50 formed within and by the umbrella shaped member 48. The proximal end 54 of the umbrella shaped member 48 is fixedly attached to the outer 22 sidewall 20 of the inner tubular member 18. The expandable perimeter on the umbrella shaped member 48 are free outer ends 52 opposite the proximal ends 54. The inflatable umbrella shaped balloon 50 within the umbrella shaped member 48 is operational between inflated 56 and deflated 58 conditions. When inflated, the inflatable umbrella shaped balloon 50 erects and shapes the umbrella shaped member 48 and seats the outer surface 60 of the umbrella shaped member 48 against the inside wall 14 and neck 12 of bladder 16 to prevent leaking. In addition, for insertion of the device 10 a dissolvable gel cap 49 is used to encapsulate the outer surface 60 of the umbrella shaped member 48, as illustrated in FIGS. 5 and 6. To inflate the inflatable umbrella shaped balloon 50 an inflation conduit 19 extends between the inflatable umbrella shaped balloon 50 and the outer end 23 of the inner tubular member 18. The coupling member 70 contains a coupling 27 for connecting the inflation conduit 19 in the inner tubular member 18 to the inflation conduit 28 in the coupling member 70. As part of the coupling member 70, a check valve 79 is connected to the inflation conduit 28 thereby providing fluid communication to the inflatable umbrella shaped balloon 50. Thus, by use of a syringe or any other injectable means, saline is injected through the insert 83 in the check valve 79 and through inflation conduits 28 and 19 to inflate the inflatable umbrella shaped balloon 50. The coupling member 70 also includes a passageway 72 with an inner sidewall surface 74 for passing urine there-through. The coupling member 70 also has an inflatable balloon valve 76 positioned within the passageway 72 of the coupling member 70 for selectively passing urine there-through. The inflatable balloon valve 76 is attached about the entire circumference 78 of the inner sidewall surface 74 of the passageway 72. When the inflated balloon valve 76 is in the normally closed inflated 80 position, the inflatable balloon valve 76 is expanded radially inward away from the inner surface 74 of the passageway 72 toward the center 82 of the passageway 70 in sealing engagement with itself. The inflatable balloon valve 76 in the inflated position 80 prevents urine from passing through the passageway 72 from within the bladder 16.

Figure 7:
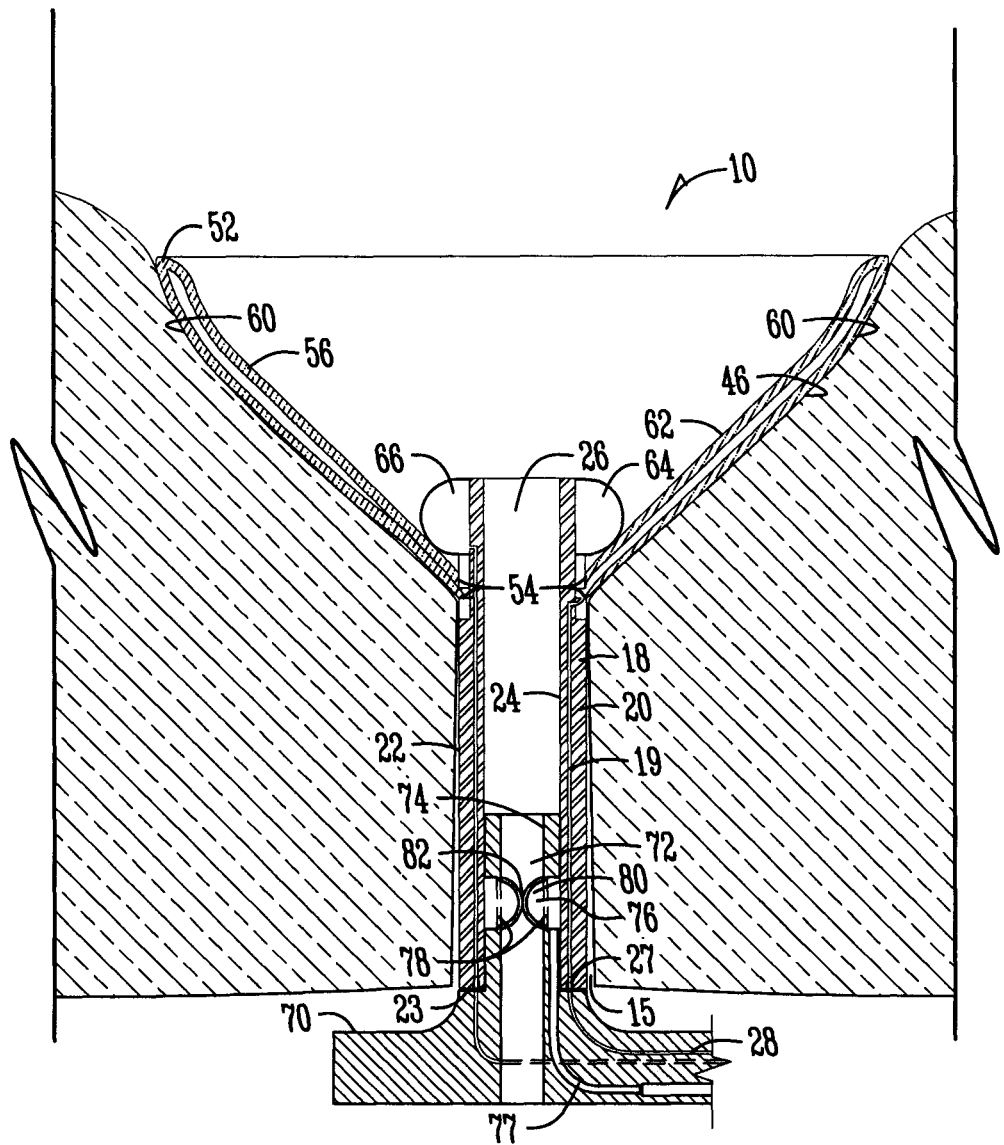
FIG. 7 is a cross-sectional view of another embodiment of the control device positioned in a bladder with the umbrella member having been fully expanded.

A second inflatable balloon 64 is positioned at the inner end 25 and around the outer sidewall 22 of the inner tubular member 18 for operation between inflated 66 and deflated 68 conditions. As best illustrated by FIG. 7, the second inflatable balloon 64 when inflated 66 presses against the inner surface 62 of the umbrella shaped member 48 to help retain the device 10 within the bladder 16 thereby maintaining sealing engagement between the outer surface 60 of the umbrella shaped member 48 and the inside wall 14 and the neck 12 of the bladder 16 to prevent leaking. To expand or inflate the second inflatable balloon 64 a second inflation conduit 21 extends between the second inflatable balloon 64 and the outer end 23 of the inner tubular member 18. A coupling member 70 is inserted into the outer end 23 of the inner tubular member 18 after the inner tubular member 18 is measured and cut to the length of the urethra 15. The second inflatable balloon 64 is inflated 66 using the second inflation conduit 21. The coupling member 70 contains a coupling 27 for connecting the second inflation conduit 21 in the inner tubular member 18 to the inflation conduit 28 in the coupling member 70. As part of the coupling member 70, a check valve 79 is connected to the inflation conduit 28 thereby providing fluid communication to the second inflatable balloon 64. Thus, by use of a syringe or any other injectable means, saline is injected through the insert 83 in the check valve 79 and through the inflation conduits 28 and 21 to inflate the inflatable balloon 30. The coupling member 70 is used to selectively pass urine through the passageway 72 of the coupling member 70. After the device 10 is inserted and the gel cap 49 dissolves the inflatable umbrella shaped balloon 50 is inflated using the inflation conduit 19. During inflation of the inflatable umbrella shaped balloon 50 the free outer ends 52 of the umbrella shaped member 48 expand radially outward from the collapsed closed shape 58 thereby sealing the outer surface 60 of the umbrella shaped member 48 against the inside wall 14 and the neck 12 of the bladder 16 to prevent leaking. The second inflatable balloon 64 is also expanded and presses against the inner surface 62 of the umbrella shaped member 48 to help retain the device 10 within the bladder 16.

Figure 8:
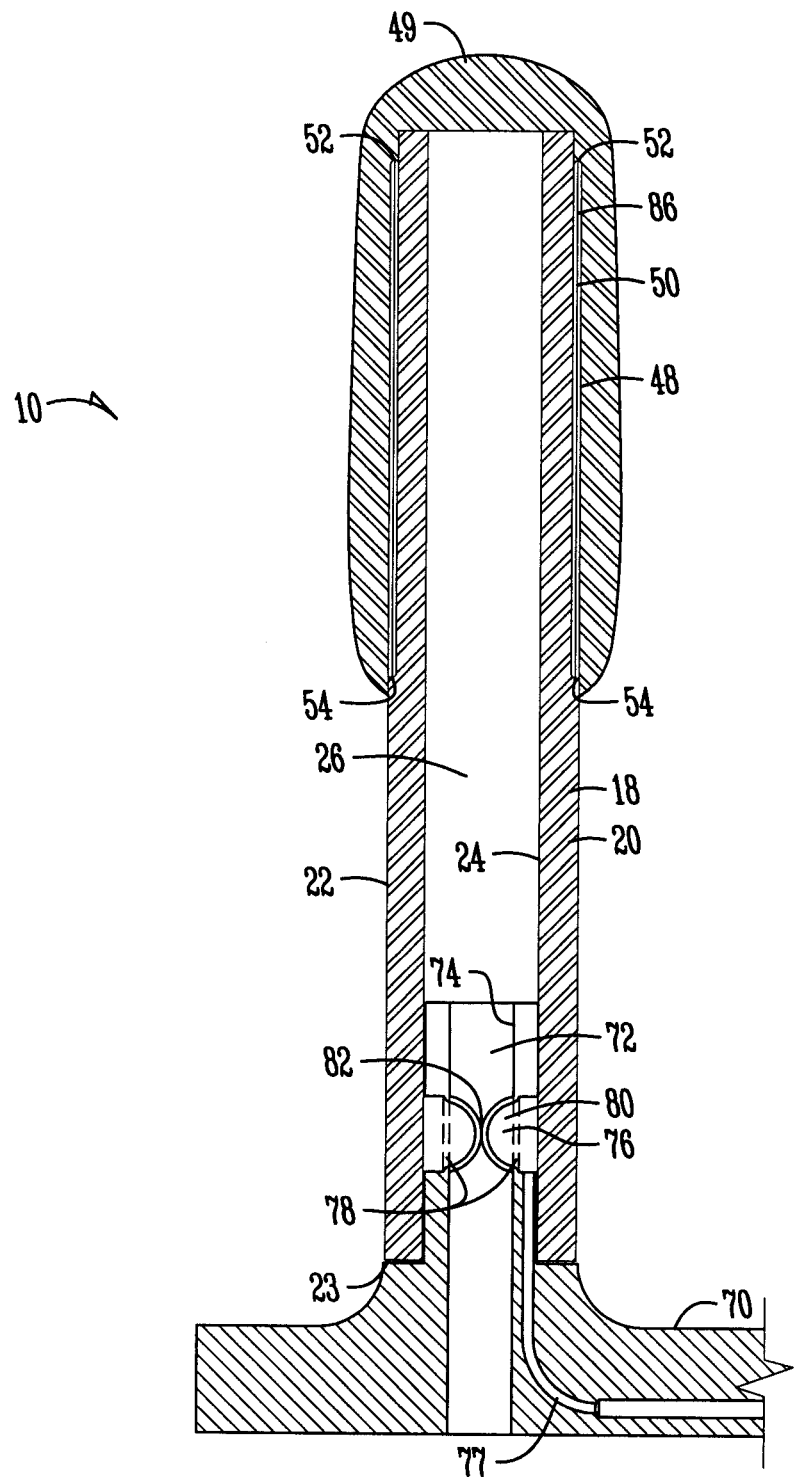
FIG. 8 is a front view of an additional embodiment of the control device.
Figure 9:
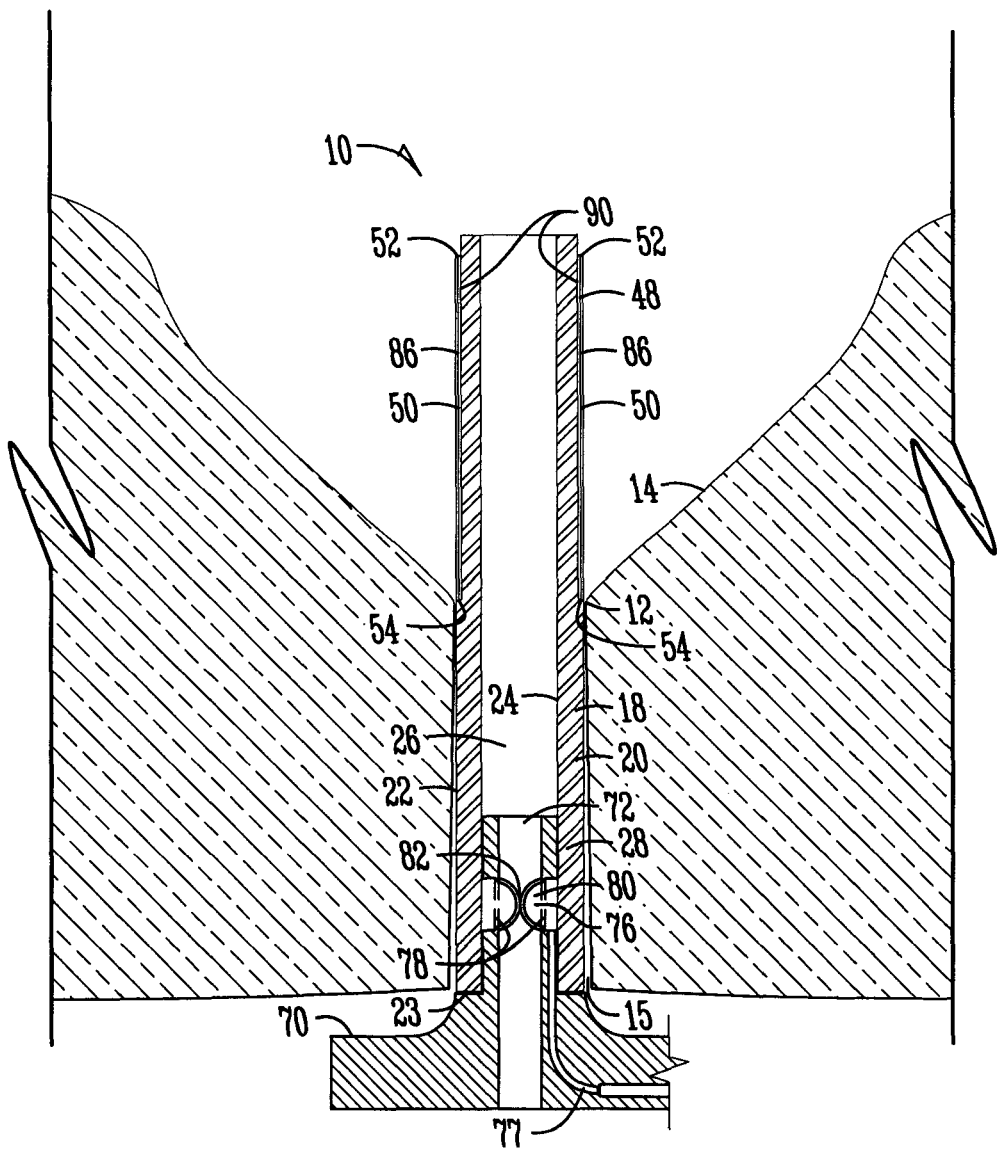
FIG. 9 is a cross-sectional view of an additional embodiment of the control device positioned in a bladder.
Figure 10:
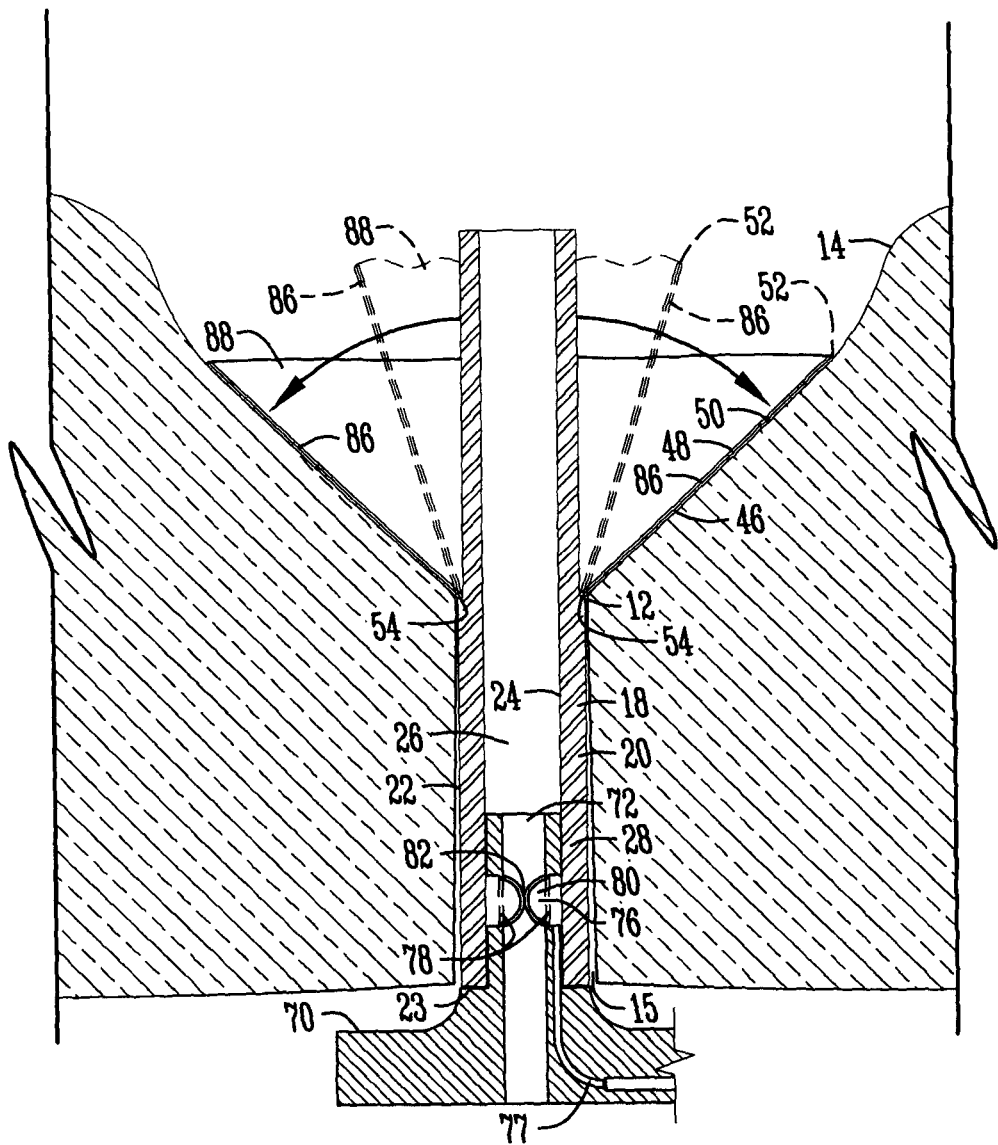
FIG. 10 is a cross-sectional view of an additional embodiment of the control device positioned in a bladder with the umbrella member having been fully expanded.

FIG. 8 is a front view of an additional embodiment of the control device. In FIG. 8, the expandable ceiling member is an umbrella shaped member 48 and the deployable stiffening member 50 is a wire frame 86 positioned within the umbrella shaped member 48. The umbrella shaped 48 is attached at its proximal end 54 to the outer 22 sidewall 20 of the inner tubular member 18. Opposite the proximal ends 54 are free outer ends 52 on the umbrella shape 48. The wire frame 86 positioned within the umbrella shaped member 48 is operational between collapsed 90 and expanded 88 conditions. The normally open wire frame 86 within the umbrella shaped member 48 is encapsulated using the gel cap 49 in the collapsed condition 90. Thus, after insertion, the gel cap 49 dissolves (See FIG. 9) and the wire frame 86 expands to its normally open position 88 thereby erecting and shaping the umbrella shaped member 48 to seat the outer surface 60 of the umbrella shaped member 48 against the inside wall 14 and neck 12 of the bladder 16, as best illustrated by FIG. 10.

Figure 11:
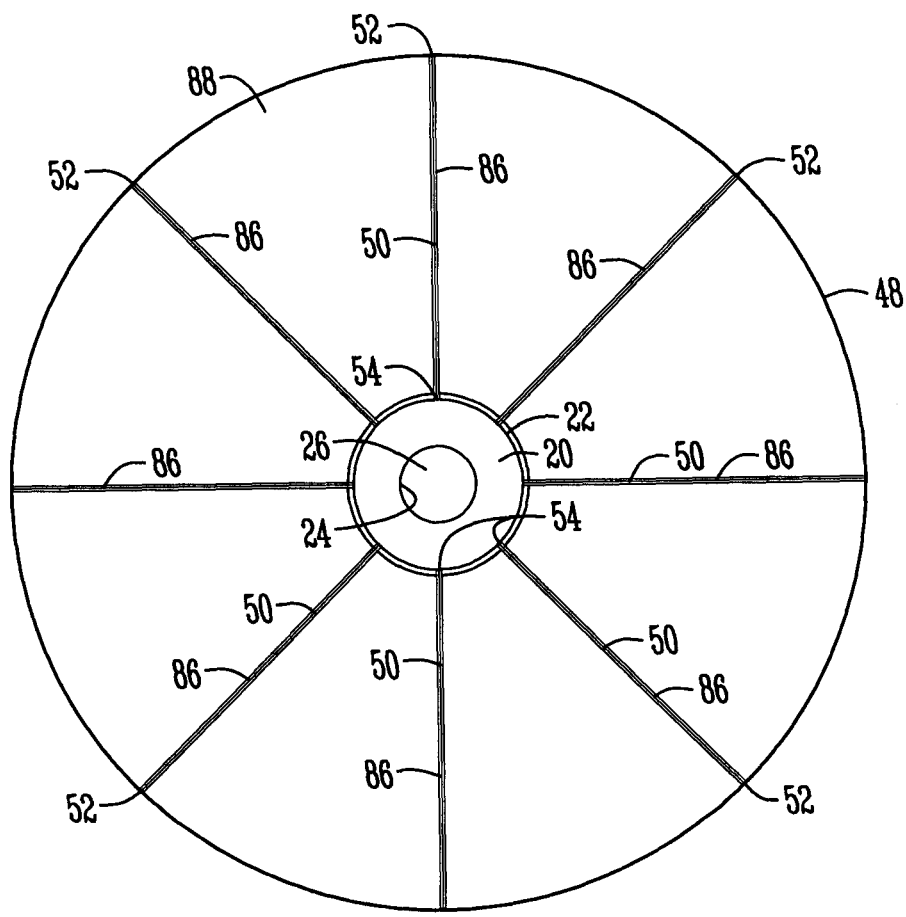
FIG. 11 is a top plan view of an additional embodiment of the control device positioned in a bladder with the umbrella member having been fully expanded.

FIG. 11 is a top plane view of the wire frame 86 within the umbrella shaped member 48 and in the expanded position 88. The wire frame 86 within the umbrella shaped member 48 is a continuous wire frame that is by default in the expanded open position 88 before being encapsulate in the gel cap 49. The wire frame 86 causes the umbrella shape member 48 to expand radially outward from the collapsed closed shape 58 being coaxial with the inner tubular member 18. The material used to construct the wire frame 86 is preferably titanium or nitinol.

Similar to the previous embodiments, a coupling member 70 is inserted into the outer end 23 of the inner tubular member 18 for selectively passing urine from within the bladder 16 through the inner tubular member 18 and the passageway 72 in the coupling member 70. The inflatable balloon valve 76 within the passageway 72 of the coupling member 70 is operated using a pump 84, as best illustrated by FIG. 12 and FIG. 13.

Figure 12:
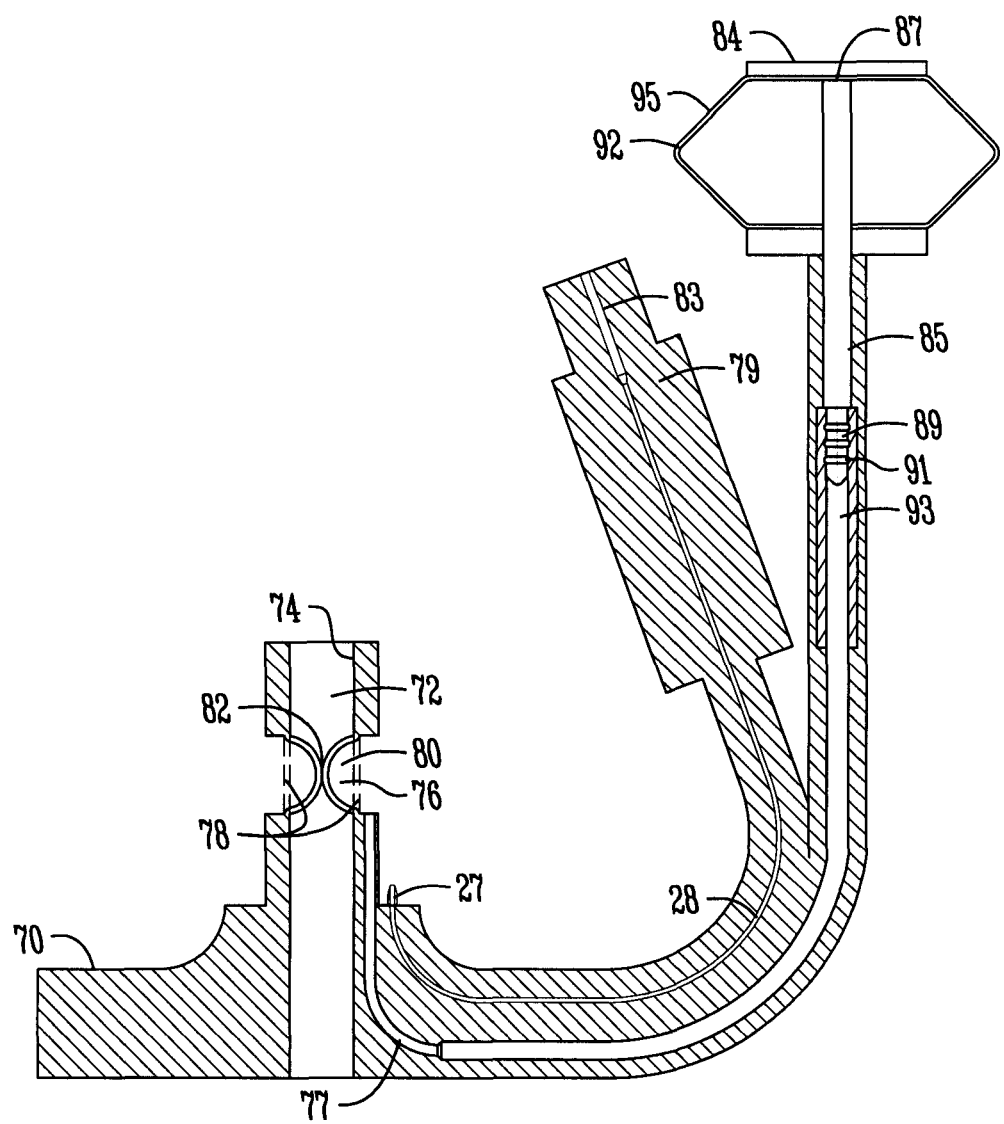
FIG. 12 is a front view of the coupling device with balloon valve and pump in the normally closed position.
Figure 13:
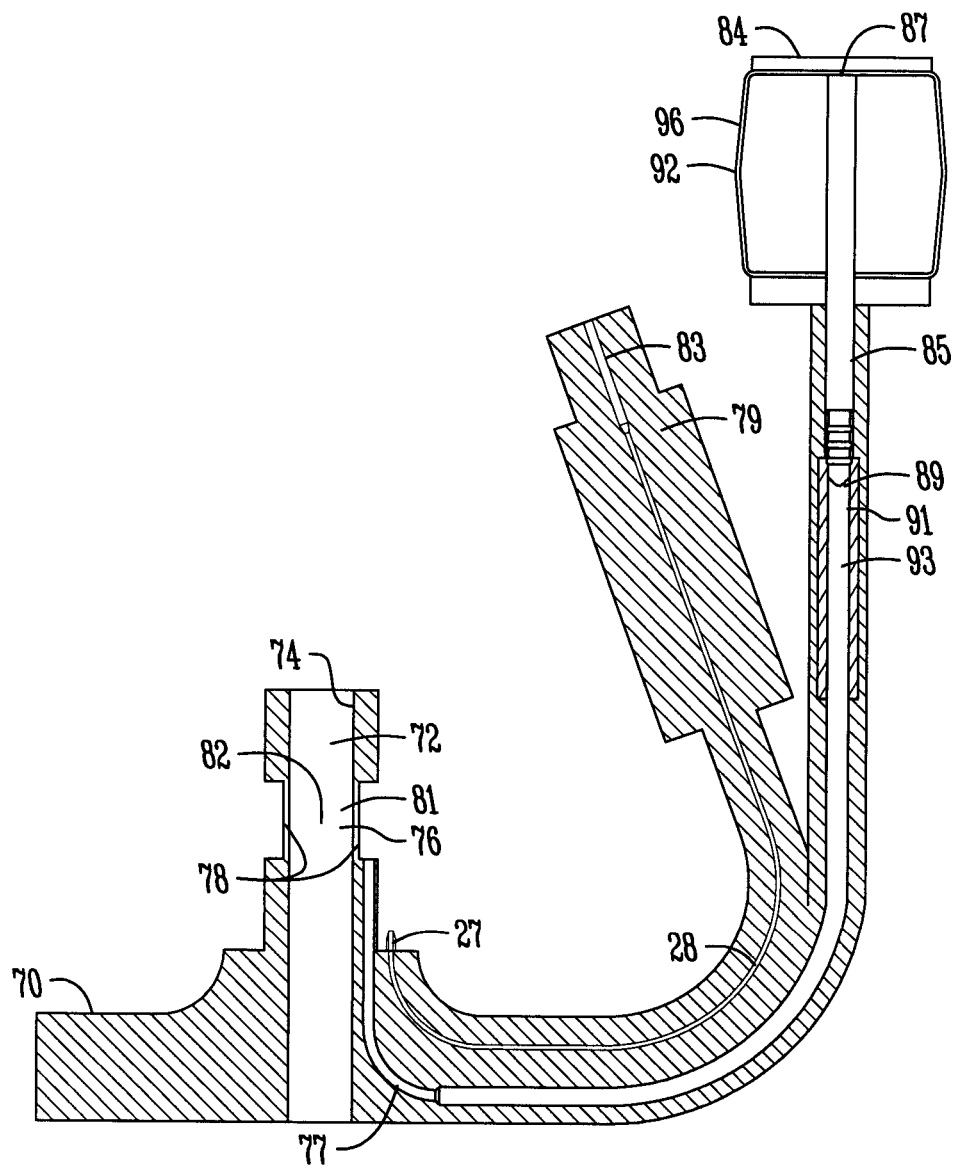
FIG. 13 is a front view of the coupling device with balloon valve and pump in the open position.

In FIG. 12 the inflatable balloon valve 76 is in the default, inflated closed position 80. In the inflated closed position 80 the inflatable balloon valve 76 is expanded radially inward away from the inner sidewall surface 74 toward the center 82 of the passageway 72 in sealing engagement with itself. The inflated position 80 of the inflatable balloon valve 76 prevents urine from passing from the inside of the bladder 16. The inflatable balloon valve 76 is deflated to its deflated condition 81 by connecting pump 84 and disengaging plunger 85. As shown in FIG. 13, disengagement of pump 84 causes the plunger 85 to retract drawing saline from within the inflatable balloon valve 76 into the plunger 85 thereby deflating the inflatable balloon valve 76 to a deflated position 81 coaxial with the inner sidewall surface 74 of the passageway 72 for passing urine through the passageway 72. The inflatable balloon valve 76 is re-inflated by releasing or no longer squeezing or pressing the living hinges 92 whereby the living hinges 92 flex outward from the pump 84 body causing the plunger 85 to move downward within the pump 84 to re-inject saline and thereby cause the inflatable balloon valve 76 to expand radially inward away from the inner sidewall surface 74 toward the center 82 of the passageway 72 in sealing engagement with itself to prevent the passage of urine through the passageway 72. The pump 84 is connected to the coupling member 70 and has a pump body. The pump body is preferably constructed of silicon rubber or a like material. The pump 84 has a pump casing 93 in fluid communication with the inflation conduit 77 and inflatable balloon valve 76. The pump 84 utilizes a pair of living hinges 92 that control the deformation and transition of the pump body from an open position 96 to a normally closed position 95.

The term "living" in living hinges 92 refers to the hinges 92 natural preference to remain in or move to the default position in which the hinges 92 are extended outward away from the pump body (in the closed position 95) and the plunger 85 being pressed into the pump casing 93. The living hinges 92 keep a constant downward pressure on the plunger 85 thereby keeping the inflatable balloon valve 76 expanded and in the closed position 80.

The pump body is connected to the plunger 85 at the first end 87 of the plunger 85. The second opposite end 89 of the plunger 85 has ribs 91 for creating a seal between the second end 89 of the plunger 85 and the pump casing 93. The living hinges 92, plunger 85 and pump casing 93 are preferably constructed of a thermoplastic or like material. The living hinges 92 are by default and at all times in the closed position 95, unless manipulated to the open position 96 (See FIG. 13). In the closed position 95, the living hinges 92 are resting in a flexed outward extended position from the pump body and plunger 87. In the closed position 95, the living hinges 92 keep the plunger 89 depressed within the pump casing 93. Keeping the plunger 89 depressed within the pump casing 93 keeps the inflatable balloon valve 76 in the inflated closed condition 80 due to the pressure the living hinges 92 exert on the plunger 85 and the plunger 85 in-turn exerts on the fluid within the pump casing 93 and inflation conduit 77. Thus, in FIG. 12, the pump 84 is shown in the closed position 95 as is the inflatable balloon valve 76. The coupling member 70 consists also of a check valve 79 having an insert 83 for a syringe. The check valve 79 is in fluid communication with inflation conduit 28, which by way of coupling 27 allows connection to inflation conduits associated with any of the embodiments of the control device, as illustrated in FIGS. 1-7. Multiple check valves 79 may be used if multiple inflation conduits 28 are needed to separately inflate different inflatable balloons associated with the different embodiments (See for example FIG. 7).

As shown in FIG. 13, deflation of the inflatable balloon valve 76 is accomplished by squeezing or pressing the living hinges 92 inward toward the body or plunger 87 of the pump 84 and holding the living hinges 92 in the open position 96. In the open position 96, the living hinges 92 are parallel to each other and the plunger 87. In the open position 96, the plunger 85 is retracted outwardly from the pump casing 93 thereby evacuating fluid from within the inflatable balloon valve 76 into the pump casing 93. Drawing fluid into the pump casing 93 evacuates the fluid from the inflatable balloon valve 76 thereby deflating the inflatable balloon valve 76 to an open deflated position 81. In the open deflated position 81, the inflatable balloon valve 76 is coaxial with the inner sidewall surface 74 of the passageway 72 for passing urine through the passageway 72. The inflatable balloon valve 76 is re-inflated by releasing or no longer squeezing or pressing the living hinges 92 inward toward the body or plunger 87 of the pump 84. The natural inclination of the living hinges 92, when released, cause the living hinges 92 to bow outward away from the body or plunger 87 of the pump 84. The movement of the living hinges 92 outward away from the body or plunger 87 of the pump 84 forces the plunger 85 downward into the pump casing 93 thereby re-introducing fluid into the inflatable balloon valve 76 so that the inflatable balloon valve 76 is inflated to its inflated closed condition.

The present invention has been shown and described above with the preferred embodiments, and it is understood that any modifications, substitutions, and additions may be made which are within the intended spirit and scope of the invention. From the foregoing, it can be seen that the present invention accomplishes at least all of its stated objects.

What is claimed is:

1. A urinary control device for sealing off at a neck and along the inside wall of a bladder to prevent leaking and dislodging of the device from within the bladder, the device comprising:

an inner tubular member having an inner and an outer end interconnected by a passageway, the inner tubular member having an inner and outer sidewall;

an expandable sealing member having an inner surface, an outer surface, a proximal end fixedly attached to the outer sidewall of the inner tubular member, and an expandable perimeter operational between a collapsed closed shape being coaxial with the inner tubular member and an expanded open shape to seal the outer surface of the expandable sealing member against the inner wall and neck of the bladder for preventing urine from leaking from the bladder;

a deployable stiffening member positioned within the expandable sealing member, the stiffening member expanding within the expandable sealing member for erecting and shaping the expandable sealing member, the deployable stiffening member to thereby assist in strengthening the expandable sealing member, retaining the device within the bladder and sealing off the bladder against leaking; and a coupling member inserted into the outer end of the inner tubular member, wherein the coupling member further comprises an inflatable balloon valve positioned to expand inwardly from an inner sidewall surface of a passageway of the coupling member for selectively passing urine there-through.

2. The urinary control device of claim 1 wherein the expandable sealing member is an expandable outermost tubular member and the deployable stiffening member is an inflatable balloon within the outermost tubular member.

3. The urinary control device of claim 2 wherein the expandable outermost tubular member has a first and second opposite end fixedly attached to the outer sidewall of the inner tubular member.

4. The urinary control device of claim 3 wherein the expandable perimeter is an annular thinned wall portion on the outermost tubular member, the outermost tubular member having slack between the first and second opposite end to thereby assist expansion of the annular thinned wall portion radially outward and away from the outer sidewall of the inner tubular member for sealing and retaining the outermost tubular member against the neck and inner wall of the bladder.

5. The urinary control device of claim 4 wherein the inflatable balloon is positioned and expanded between the inner and outermost tubular members.

6. The urinary control device of claim 5 wherein the inner tubular member has an inflation conduit extending between the inflatable balloon and the outer end of the inner tubular member.

7. The urinary control device of claim 6 wherein the inner tubular member is measured and cut to the length of the urethra.

8. The urinary control device of claim 1 wherein the passageway of the coupling member has a center and an inner sidewall surface for passing urine there-through.

9. The urinary control device of claim 1 wherein the inflatable balloon valve is attached around a circumference of the inner sidewall surface of the passageway of the coupling member and when inflated expands radially inward away from the inner sidewall surface toward the center of the passageway of the coupling member in sealing engagement with itself.

10. The urinary control device of claim 1 wherein the coupling member has a pump and inflation conduit in fluid communication with the inflatable balloon valve for deflating the inflatable balloon valve from a normally closed position to an open position where the inflatable balloon is coaxial with the inner sidewall surface of the passageway of the coupling member for passing urine there-through.

11. The urinary control device of claim 10 wherein the pump comprises a pump casing and a pair of living hinges adapted for connection to a plunger to thereby assist movement of the plunger within the pump casing.

12. The urinary control device of claim 11 wherein the living hinges are pressed and held inward toward the plunger for drawing the plunger out of the pump casing and evacuating the inflatable balloon valve thereby collapsing the inflatable balloon valve and allowing urine to pass thereby.

13. The urinary control device of claim 12 wherein the living hinges are released to flex outward away from the plunger thereby pushing the plunger into the pump casing and inflating the inflatable balloon valve to prevent urine to pass thereby.

14. The urinary control device of claim 1 wherein the coupling member further comprises at least one check valve having at least one inflation conduit in fluid communication with the inflatable balloon for inflating the balloon.

15. A method for sealing off at a neck and along the inside wall of a bladder using a urinary control device to prevent leaking and dislodging of the device from within the bladder, the method comprising:
providing an inner tubular member having an inner and an outer end interconnected by a passageway, the inner tubular member having an inner and outer sidewall;
expanding an expandable sealing member having an inner surface, an outer surface, a proximal end fixedly attached to the outer sidewall of the inner tubular member, and an expandable perimeter on the sealing member operational between a collapsed closed shape being coaxial with the inner tubular member and an expanded open shape to seal the outer surface of the expandable sealing member against the inner wall and neck of the bladder for preventing urine from leaking from the bladder;
deploying a deployable stiffening member positioned within the expandable sealing member, the stiffening member expanding within the expandable sealing member for erecting and shaping the expandable sealing member, the deployable stiffening member to thereby assist in strengthening the expandable sealing member, retaining the device within the bladder and sealing off the bladder against leaking; and
inserting a coupling member into the outer end of the inner tubular member, wherein the coupling member further comprises an inflatable balloon valve positioned to expand inwardly from an inner sidewall surface of a passageway of the coupling member for selectively passing urine there-through.

16. The method of claim 15 wherein the stiffening member comprises an inflatable balloon at the inner end and around the outer sidewall of the inner tubular member for operation between inflated and deflated conditions, the inflatable balloon when inflated pressing against the inner surface of the expandable sealing member for retaining the device within the bladder and maintaining sealing engagement between the outer surface of the expandable sealing member and the inside wall and neck of the bladder to prevent leaking.

17. The method of claim 16 wherein the inner tubular member is measured and cut to the length of the urethra.

18. The method of claim 15 wherein the inflatable balloon valve is attached around a circumference of the inner sidewall surface of the passageway of the coupling member and when inflated expands radially inward away from the inner sidewall surface toward a center of the passageway of the coupling member in sealing engagement with itself.

19. The method of claim 15 wherein the coupling member has a pump and inflation conduit in fluid communication with the inflatable balloon valve for deflating the inflatable balloon valve from a normally closed position to an open position where the inflatable balloon is coaxial with the inner sidewall surface of the passageway of the coupling member for passing urine there-through.

20. The method of claim 19 wherein the pump comprises a pump casing and a pair of living hinges adapted for connection to a plunger to thereby assist movement of the plunger within the pump casing.

21. The method of claim 20 wherein the living hinges are pressed and held inward toward the plunger for drawing the plunger out of the pump casing and evacuating the inflatable balloon valve thereby collapsing the inflatable balloon valve and allowing urine to pass thereby.

22. The method of claim 21 wherein the living hinges are released to flex outward away from the plunger thereby pushing the plunger into the pump casing and inflating the inflatable balloon valve to prevent urine to pass thereby.

23. The method of claim 15 wherein the coupling member further comprises at least one check valve having at least one inflation conduit in fluid communication with the inflatable balloon for inflating the balloon.

* * * * *